(12) United States Patent
Segner et al.

(10) Patent No.: US 7,951,091 B2
(45) Date of Patent: May 31, 2011

(54) GUIDE WIRE WITH STRANDED TIP

(75) Inventors: Garland L. Segner, Delano, MN (US);
Kent D. Anderson, Champlin, MN
(US); Douglas B. P. Molland, Tonka
Bay, MN (US); Thomas L. Clubb,
Hudson, WI (US); Michael J. Urick, St.
Paul, MN (US)

(73) Assignee: Tyco Healthcare Group LP, Mansfield,
MA (US)

( * ) Notice: Subject to any disclaimer, the term of this
patent is extended or adjusted under 35
U.S.C. 154(b) by 1591 days.

(21) Appl. No.: 10/632,145

(22) Filed: Jul. 31, 2003

(65) Prior Publication Data

US 2005/0027212 A1 Feb. 3, 2005

(51) Int. Cl.
*A61M 25/00* (2006.01)
(52) U.S. Cl. ...................................................... 600/585
(58) Field of Classification Search .................. 600/585
See application file for complete search history.

(56) References Cited

U.S. PATENT DOCUMENTS

| | | | |
|---|---|---|---|
| 3,612,058 A | 10/1971 | Ackerman et al. | |
| 4,579,127 A | 4/1986 | Haacke | |
| 4,611,390 A | 9/1986 | Tanaka et al. | |
| 4,682,607 A | 7/1987 | Vaillancourt et al. | |
| 4,763,647 A * | 8/1988 | Gambale | 600/434 |
| 4,876,126 A | 10/1989 | Takemura et al. | |
| 4,925,445 A | 5/1990 | Sakamoto et al. | |
| 4,945,342 A | 7/1990 | Steinemann | |
| 5,025,799 A | 6/1991 | Wilson | |
| 5,067,489 A | 11/1991 | Lind | |
| 5,129,890 A | 7/1992 | Bates et al. | |
| 5,165,421 A * | 11/1992 | Fleischhacker et al. | 600/585 |
| 5,217,026 A | 6/1993 | Stoy et al. | |
| 5,251,640 A | 10/1993 | Osborne | |
| 5,344,315 A | 9/1994 | Hanson | |
| 5,386,828 A | 2/1995 | Owens et al. | |
| 5,497,783 A | 3/1996 | Urick et al. | |
| 5,514,128 A | 5/1996 | Hillsman et al. | |
| 5,520,194 A * | 5/1996 | Miyata et al. | 600/585 |
| 5,749,837 A * | 5/1998 | Palermo et al. | 600/585 |
| 5,827,201 A | 10/1998 | Samson et al. | |
| 5,897,584 A | 4/1999 | Herman | |
| 6,019,736 A * | 2/2000 | Avellanet et al. | 600/585 |

(Continued)

FOREIGN PATENT DOCUMENTS

EP 1 243 283 A2 9/2002

(Continued)

OTHER PUBLICATIONS

Nov. 8, 2004 Invitation to Pay Additional Fees and Partial International Search Report in PCT/US2004/020042 (4 pages).

(Continued)

*Primary Examiner* — Jeffrey G Hoekstra
(74) *Attorney, Agent, or Firm* — Popovich, Wiles &
O'Connell, P.A.

(57) ABSTRACT

A guide wire comprising an elongate, flexible core having a proximal region, a proximal end, a distal region, and a distal end, and the distal region having a tapered portion; a plurality of wire strands wrapped helically parallel to one another and disposed on at least a portion of the tapered distal region of the core; a polymer tie layer disposed on at least a portion of the plurality of wire strands; and a lubricious polymer layer disposed on the polymer tie layer.

39 Claims, 8 Drawing Sheets

U.S. PATENT DOCUMENTS

| | | | |
|---|---|---|---|
| 6,159,165 | A | 12/2000 | Ferrera et al. |
| 6,165,140 | A | 12/2000 | Ferrera |
| 6,168,570 | B1 | 1/2001 | Ferrera |
| 6,191,365 | B1 * | 2/2001 | Avellanet .................. 174/128.1 |
| 6,399,886 | B1 | 6/2002 | Avellanet |
| 6,432,066 | B1 | 8/2002 | Ferrera |
| 6,475,169 | B2 | 11/2002 | Ferrera |
| 6,805,676 | B2 | 10/2004 | Klint |
| 6,881,194 | B2 | 4/2005 | Miyata et al. |
| 7,070,608 | B2 | 7/2006 | Kurz et al. |
| 2001/0021831 | A1 | 9/2001 | Fleischhacker et al. |
| 2001/0023325 | A1 | 9/2001 | Ferrera |
| 2002/0045885 | A1 | 4/2002 | Cornelius et al. |
| 2002/0151823 | A1 | 10/2002 | Miyata et al. |
| 2002/0193706 | A1 | 12/2002 | Ferrera et al. |
| 2004/0243168 | A1 * | 12/2004 | Ferrera et al. ................. 606/191 |
| 2007/0010762 | A1 | 1/2007 | Ressemann et al. |

FOREIGN PATENT DOCUMENTS

| | | |
|---|---|---|
| EP | 1 277 447 A2 | 1/2003 |
| WO | WO 92/13483 | 8/1992 |
| WO | WO 99/29260 | 6/1999 |

OTHER PUBLICATIONS

Feb. 18, 2005 Notification of Transmittal of the International Search Report and the Written Opinion of the International Searching Authority, or the Declaration in PCT/US2004/020042 (17 pages).

* cited by examiner

GUIDE WIRE WITH STRANDED TIP

FIELD OF THE INVENTION

This invention relates to a guide wire for use in surgical intervention procedures. In particular, this invention relates to a guide wire with a distal tip having multiple filaments.

BACKGROUND OF THE INVENTION

Guide wires are generally elongate structures for use in medical procedures. During such procedures, a distal portion of the wire is positioned within a lumen of a patient's body to acquire and/or maintain access to a region of interest. For example, such a region of interest of a patient's body may include a locally stenosed lumen at a location in the patient's vascular system. A catheter can be advanced over a guide wire for treatment or diagnostic purposes.

The guide wire and catheter are positioned within the patient's body by an operator such as a medical doctor. A proximal portion of the wire and a proximal portion of the catheter extend outwardly from the patient's body for manipulation by the operator. The operator steers the guide wire to a treatment site by forming a small bend on the distal end of the wire, introducing the wire percutaneously into the patient's body, and advancing and torqueing the guide wire until the region of interest is reached. The guide wire can be directed into an off-axis channel by torqueing the wire until the bent tip enters the channel and then advancing the guide wire further into the channel. In the case of over-the-wire systems, at least a portion of the wire must extend proximally relative to the proximal end of the catheter, thereby allowing the catheter to be manipulated axially relative to the wire.

Guide wires may be maintained at an intended axial position within the lumen of the patient's body so as to afford access to a treatment or diagnostic site. The wire may be maintained by any means that enable the relative position of the wire to be established within the lumen, such as by an anchored distal protection device, or by manually maintaining the position of the wire within the lumen. Once an axial position is established, the wire is maintained in position to allow devices such as a balloon catheter, a stent, a distal protection device, an atherectomy catheter, a thrombectomy catheter, or the like to be advanced over the wire to the treatment or diagnostic site.

Guide wires have several key performance requirements. Flexibility is needed for adequate tracking in tortuous anatomy. Flexibility and control of movement is particularly desirable at the distal end of a guide wire. The guide wire preferably has isotropic bending characteristics along the proximal shaft region to prevent occurrence of whipping during application of torque. In addition, the guide wire needs good structural integrity so that it does not bend undesirably, kink, or pull apart in tension. Guide wires need to have good torsional stiffness along their entire length so they can be steered into a region of interest by application of torque. At least a portion of a guide wire needs to be radiopaque so that it can be viewed fluoroscopically during an interventional procedure.

Guide wires often include a "floppy tip" at their distal end. The floppy distal tip provides an atraumatic and radiopaque terminus and can be any desired length. An atraumatic tip prevents vessel injury during initial placement or subsequent advancement of the guide wire. A radiopaque tip helps the physician verify suitable tip placement during fluoroscopy. The floppy tip can comprise a springy or resilient material, such as a metal (e.g., stainless steel, iron alloys such as Elgiloy™, and shape memory metal such as nitinol) or polymer (e.g., polyetheretherketone (PEEK), polyimide, polyester, PEBAX, urethane, polytetrafluoroethylene (PTFE), and the like). Springy materials are desirable because they tend to retain their shape. The physician will initially shape the tip, typically with a slight curve, and then as the wire is advanced through the body the tip will be deflected as it encounters obstacles. It is desirable, after the inevitable deflections during insertion, that the tip restores itself to the pre-set shape.

The transition between a guide wire and its distal tip is most preferably smooth and continuous to promote pushability and tracking. State of the art guide wires employ various distal tips which include radiopaque coils and sheaths. Frequently, coil tips are bonded or welded to the distal end of the guide wire, resulting in stiffened areas that affect the flexibility and handleability of the guide wire. An added disadvantage is that coils require an attachment method such as welding, soldering, or adhesive bonding, which can adversely affect fluoroscopic tracking. Radiopaque sheathed tips can also result in undesirable stiffness at the distal end of a guide wire. Further, conventional coiled guide wire tips are not strong in tension and it is not unusual for a guide wire tip to separate from the guide wire during use. Tip separation is often accompanied by lengthening and unwinding of the coil which offers minimal resistance to tensile forces due to the fact that the coil turns are substantially transverse to the coil axis. Although safety wires are often added to guide wire tips to prevent coil lengthening, such wires must be small in cross section to prevent adding unwanted stiffness to the tip of the guide wire. Because their cross-sectional area must be low, the strength of safety wires is limited.

Still needed in the art are guide wires that are particularly easy to advance and control and are flexible for their entire length yet which are sufficiently strong in tension to prevent damage during use. In particular, a more flexible and torquable distal end of the guide wire would be desirable.

SUMMARY OF THE INVENTION

The invention provides a guide wire comprising an elongate, flexible core having a proximal region, a proximal end, a distal region, and a distal end, and the distal region having a tapered portion; a plurality of wire strands wrapped helically parallel to one another and disposed on at least a portion of the tapered distal region of the core; a polymer tie layer disposed on at least a portion of the plurality of wire strands; and a lubricious polymer layer disposed on the polymer tie layer.

The invention also provides a guide wire comprising an elongate, flexible core having a proximal region, a proximal end, a distal region, and a distal end, and the distal region having a tapered portion; a plurality of wire strands wrapped helically parallel to one another and disposed on at least a portion of the tapered distal region of the core; and a polymer tie layer disposed on at least a portion of the plurality of wire strands. The polymer tie layer provides the only form of attachment between the plurality of wire strands and the core.

It is to be understood that both the foregoing general description and the following detailed description are exemplary and explanatory and are intended to provide further explanation of the invention as claimed.

BRIEF DESCRIPTION OF THE DRAWINGS

FIG. 1A is a cross-sectional view of one embodiment of the guide wire of this invention. FIG. 1B is a transverse, cross-sectional view of the embodiment of FIG. 1A.

FIG. 3A to 3D are cross-sectional views of other embodiments of the guide wire of this invention.

DETAILED DESCRIPTION OF THE PREFERRED EMBODIMENTS

The terms "distal" and "proximal" as used herein refer to the relative position of the guide wire in a lumen. The most "proximal" point of the guide wire is the end of the guide wire extending outside the body closest to the physician. The most "distal" point of the guide wire is the end of the guide wire placed farthest into a body lumen from the entrance site.

The guide wire of this invention is intended for use during interventional, diagnostic, and access procedures such as coronary, peripheral, neurovascular, and gastro-intestinal applications.

The guide wire of this invention can comprise a core wire, filaments or strands of various materials disposed about the core wire to produce desired characteristics of flexibility and handleability, a polymer coating disposed over the strands, and a lubricious coating disposed about at least the distal portion of the guide wire. In one embodiment, the distal tip further comprises a polymer containing radiopaque material.

Suitable materials for the guide wire include one or more of a metal, a shape memory metal alloy or polymer, stainless steel, and engineering polymers. These materials include titanium and its alloys, cobalt-chromium-nickel-molybdenum-iron alloy (commercially available under the trade designation Elgiloy™), and polymers such as liquid crystal polymers, polyetheretherketone (PEEK), polyimide, and polyester. A shape memory or superelastic metal or polymer is particularly suitable for applications in which it is desired that the guide wire maintain a pre-determined curvature. A shape memory or superelastic metal comprising nickel and titanium known as "nitinol" is commercially available in various dimensions and can be heat set into a desired shape, compressed for delivery to a site, and then released to resume the heat-set shape.

The core wire is shaped by any suitable means, typically by grinding or etching to the desired shape and dimension. For example, a desired length of the distal portion of the core wire is made narrower and/or flatter than the proximal portion of the core wire. Grinding is one preferred method to reduce the outer diameter of the core wire. It should be noted that the core wire may be provided with a lubricious coating, such as polyfluorotetraethylene (PTFE) or other fluorinated polymers, parylene, polyurethanes, and silicones. The core wire may be coated prior to or after grinding.

About the distal portion of the core wire are disposed one or more strands of a shape memory alloy or a combination of materials designed to impart the proper flexibility to the distal tip. These materials include titanium and its alloys, cobalt-chromium-nickel-molybdenum-iron alloy (commercially available under the trade designation Elgiloy™), stainless steel, tungsten, platinum, and engineered polymers such as liquid crystal polymers, polyetheretherketone (PEEK), polyimide, and polyester. These strands may be laid in the vicinity of or adjacent to the core wire. In preferred embodiments, 3 to 24 filaments or wires, having diameters ranging from 0.0025 cm (0.001 inch) to about 0.025 cm (0.010 inch) are disposed next to the core wire.

An optional polymer sheath or layer comprises one or more polymers, e.g., polyamide block copolymers (commercially available under the trade designation "PEBAX"), nylon, ethyl vinyl acetate, silicone, urethane, polytetrafluoroethylene, or polyethylene. The polymer sheath can be produced by dip coating or direct extrusion. The polymer sheath can be comprised of a piece of heat shrink tubing that is recovered onto the wire by application of heat to the tubing. The polymer sheath can be formed by placing a piece of thermoplastic tubing within a piece of heat shrink tubing on the tip of the wire and thermally reflowing the thermoplastic tubing. This is done by applying enough heat to melt the thermoplastic tubing and simultaneously recover the heat shrink tubing such that pressure applied by the heat shrink tubing forces the melted thermoplastic tubing into contact with the unmelted components of the tip. Often significant adhesion between components can be achieved using this technique. Once the polymer sheath has been applied, an additional grinding operation may be needed to obtain a consistent outer diameter over the length of the polymer sheath.

An optional lubricious coating preferably is disposed about the strands, about the polymer layer, if it is present, or about both the strands and the polymer layer. Typically, the proximal portion of the core wire will already have a lubricious coating on it and does not require further coating. Suitable lubricious coatings include hydrophilic materials such as polyvinylpyrrolidone (PVP), polyethylene oxide, polyethylene glycol, cellulosic polymers, and hydrophilic maleic anhydride, or hydrophobic materials such as silicone, PTFE, or FEP. These coatings are typically applied by dip coating or spray methods, and heat curing may be used. For example, cure temperatures up to about 70° C. are used for silicone coatings, and several hundred degrees may be required for PTFE coatings.

In addition to the lubricious coating, bioactive coatings may be applied over all or part of the guide wire. Such coatings also may incorporate materials such as heparin, hirudin and its analogs, or other drugs. These coatings typically are applied by dip coating. Bioactive coatings are desirable to prevent blood clotting or for delivery of drugs to a specific site.

An additional and optional radiopaque polymer tip section may comprise a flexible polymer such as PEBAX, polyurethane, or polyethylene having a radiopaque material in it. Such radiopaque materials are well known in the art and typically include compounds of tungsten, barium, and/or bismuth.

In the figures below, the full length of the guide wire is not shown, and it is to be understood that the length of the guide wire can vary as desired, though typically it ranges in length from 30 to 400 cm. Procedures such as Peripherally Inserted Central Catheter (PICC) placement or vascular access may require guide wires from 30 to 80 cm in length. Common lengths of guide wires for coronary, peripheral and neurovascular interventions range from 170 to 300 cm in length. These lengths allow for the use of standardized rapid exchange and over-the-wire catheter systems, respectively. The length of the shaped distal end also may vary, for example, from 5 to 80 cm in length.

The outer diameter of the guide wire ranges from about 0.013 cm (0.005 inch) to about 0.097 cm (0.038 inch). These diameters are standard for guide wires used during neurovascular, cardiovascular, peripheral, and gastrointestinal procedures. The diameter preferably remains relatively constant over the length of the guide wire, though a small amount of tapering may occur at the distal end.

The various embodiments of the invention will now be described in connection with the drawing figures. It should be understood that for purposes of better describing the invention, the drawings have not been made to scale. Further, some of the figures include enlarged or distorted portions for the purpose of showing features that would not otherwise be apparent.

Figures 1A, 1B, 3A:
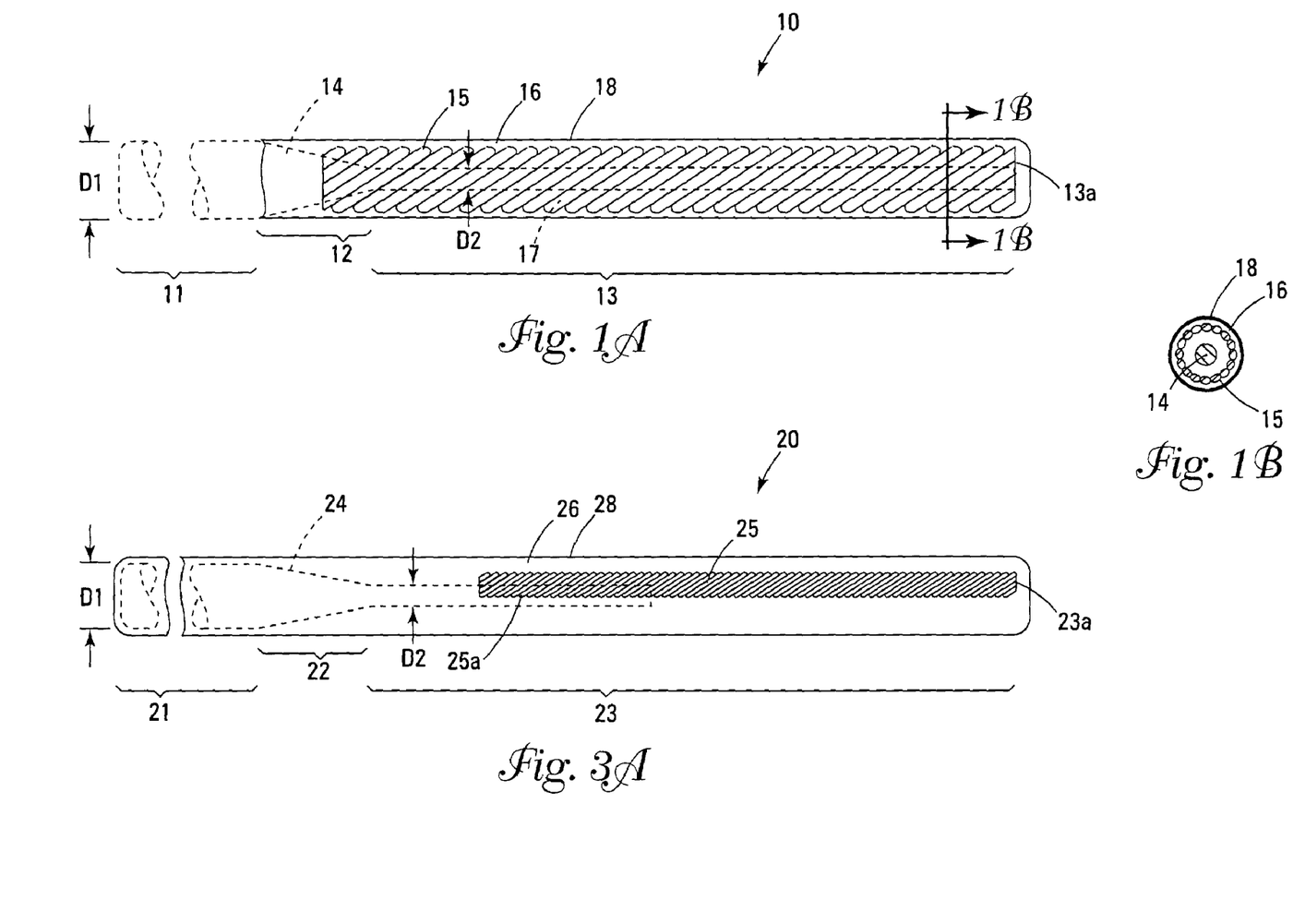
Figure 7:
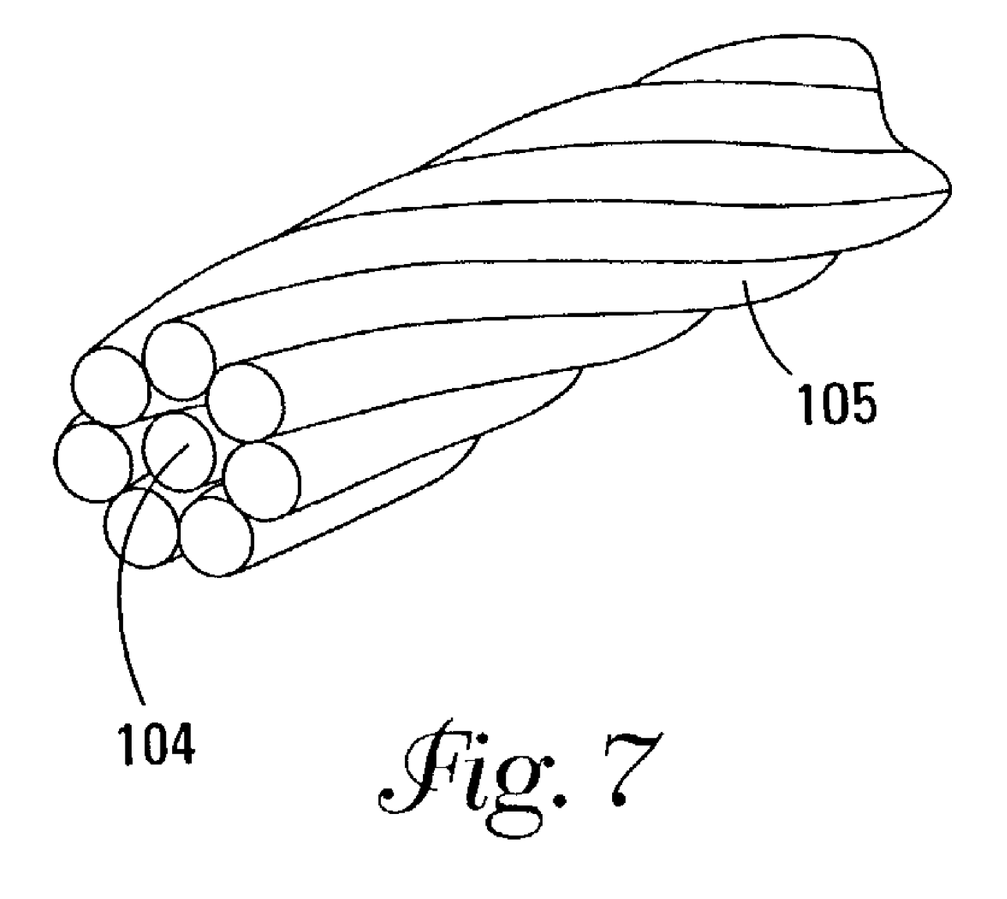
FIG. 7 is a perspective view of a section of core wire with wire strands disposed about it.

FIG. 1A illustrates a guide wire 10 comprising central core 14. In a preferred construction, core 14 comprises nitinol, NiTiCr, or an alloy of nitinol with an austenite finish temperature below room temperature. Proximal portion 11 of central core 14 has a constant diameter D1, and this tapers to smaller diameter D2 at distal portion 13, through tapering region 12. A typical diameter D1 is 0.044 cm (0.0175 inch) and a typical diameter D2 is 0.0076 cm (0.003 inch), though it is to be understood that any desirable diameter may be used. Central core 14 extends to distal tip 13a. Strands of wire 15 are disposed about distal portion 13 and tapering region 12. In one embodiment sixteen strands of 0.0064 cm (0.0025 inch) diameter nitinol wire are used, wound in a helical pattern to an overall diameter of 0.036 cm (0.014 inch) such as shown in FIG. 7 below. Helical strands of wire 15 can be attached to central core 14 using adhesive, solder, welding, by crimping a tubular band over the strands, and the like at the point where strands of wire 15 abut tapering region 12 or can be unattached to central core 14. Helical strands of wire 15 can be attached to distal tip 13a using adhesive, solder, welding, by crimping a tubular band over the strands, and the like at the point where strands of wire 15 abut central core 14 or central core enlarged distal end (described below) or can be unattached to central core 14. A cross-sectional drawing through the distal portion 13 is shown in FIG. 1B. In the example given above the wire constructed with helical strands has tremendous strength compared to wires of conventional construction where a monofilament core of approximately 0.0076 cm (0.003 inch) diameter would be used near the tip. The cross-sectional area of sixteen strands of 0.0064 cm (0.0025 inch) diameter is approximately eleven times the cross-sectional area of a core wire of 0.0076 cm (0.003 inch) diameter.

Disposed over strands 15 is polymer coating 16, covering strands 15 from tapering region 12 to tip 13a, and preferably comprises flexible polymer such as PEBAX or polyethylene. The polymer coating is applied so that the outer diameter of the distal portion is constant or may be post processed such as by grinding to achieve a diameter similar to that of proximal portion 11. Optionally, polymer coating 16 can be applied over the entire length of guide wire 10, or over a portion of guide wire 10, provided that central core proximal portion 11 is reduced in diameter to accommodate the thickness of polymer coating 16. In another embodiment, polymer coating fills some or all of the annular space 17 between central core 14 and strands of wire 15.

Disposed over polymer coating 16 is lubricious layer 18, which covers the distal-most 5 to 50 cm of the guide wire. Preferably, this lubricious layer comprises a hydrophilic coating comprised in part of maleic anhydride. However, the lubricious coating can be comprised of any of the materials described above. In another embodiment, the polymer coating can be replaced in whole or in part by a radiopaque metallic coil as is known in the guide wire arts.

Figure 1C:
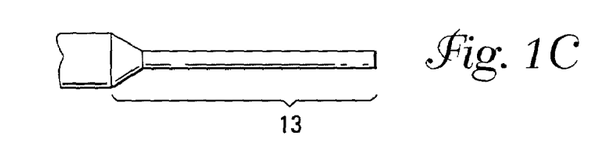
FIGS. 1C to 1J show additional embodiments of the distal portion of guide wire central core.
Figure 1D:
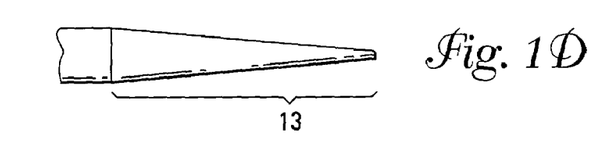
Figure 1E:
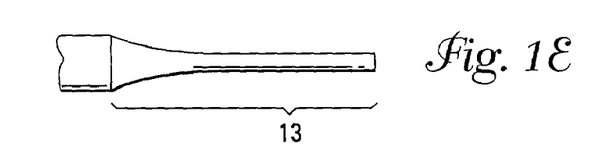
Figure 1F:
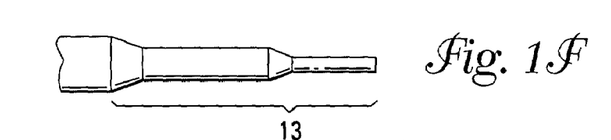
Figure 1G:
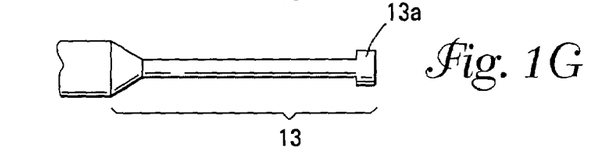

FIGS. 1C to 1J illustrate additional embodiments of the distal portion 13 of guide wire central core 14. FIG. 1C shows a constant diameter portion similar to that shown in FIG. 1A. FIG. 1D shows a linearly tapering portion. FIG. 1E shows a parabolic tapering portion. FIG. 1F shows two constant diameter portions separated by a step. It is understood that any combination of steps, tapers, and constant diameter sub-portions can be combined to comprise the distal portion 13. FIG. 1G shows an enlarged distal end. An enlarged distal end simplifies manufacturing by concentrically aligning the core with the wire strands. An elongated distal end can be combined with any design herein with a core extended to or near the distal tip. If core extends beyond the distal tip, an enlarged region can be ground into the wire proximal to the distal end of the wire. Enlarged regions proximal to the distal end of the wire are disclosed in U.S. Pat. No. 5,067,489, the contents of which are hereby incorporated by reference herein.

Figure 1H:
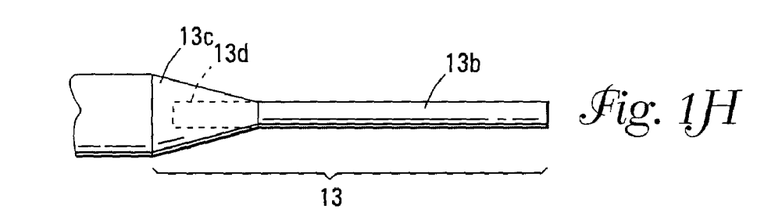
Figure 1I:
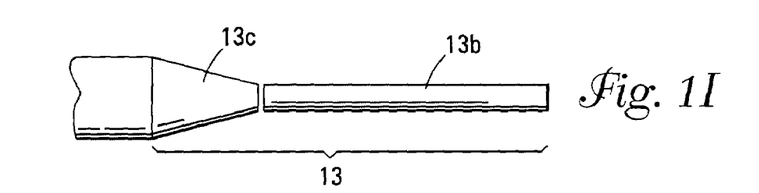
Figure 1J:
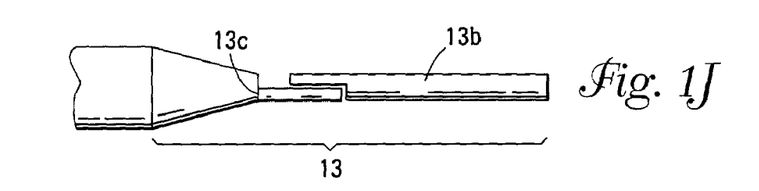

FIG. 1H shows a socket 13d in the central core portion 13c and a distal core portion 13b that floats in the socket. FIG. 1I shows central core portion 13c and distal core portion 13b arranged end to end. FIG. 1J shows a central core portion 13c and a distal core portion 13b that overlap. In FIGS. 1H to 1J, distal core portion can be metal or polymer, can be of graduated stiffness such as by joining different polymer segments end to end or by varying composition or properties along length, and can be of round, flat, ovoid, or other cross section. A particularly preferred combination is a stainless steel central core and a nitinol distal core; this wire will have adequate support along the proximal portion and good kink resistance and damage resistance in the tip region. Axial strength is provided by the outer layer of strands in these socket designs.

Figure 2:
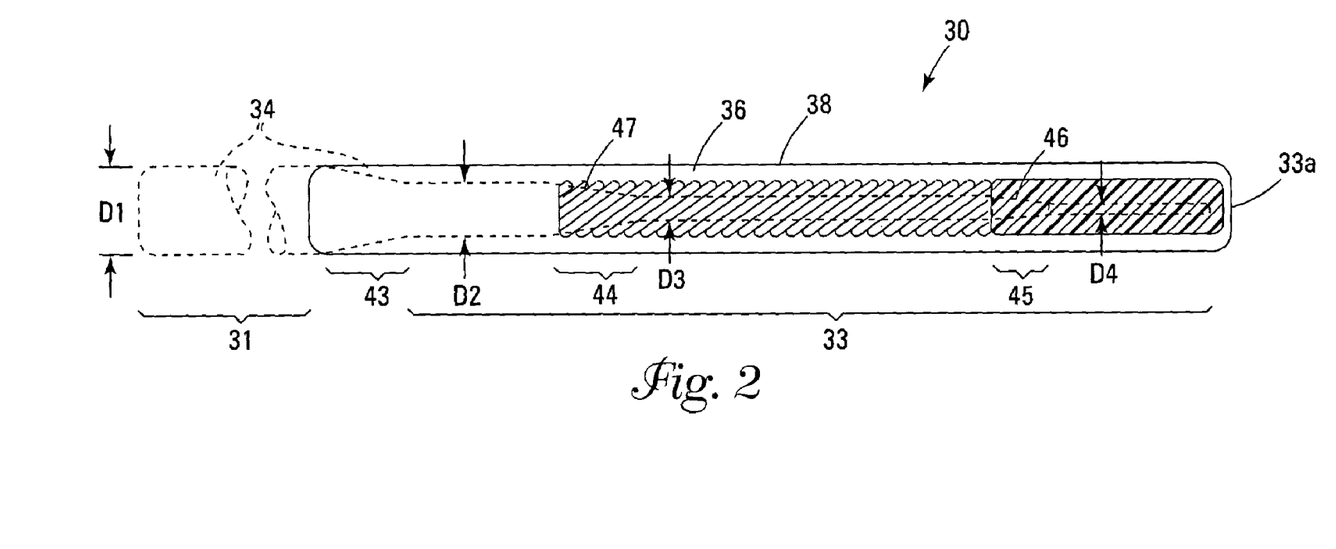
FIG. 2 is a cross-sectional view of another embodiment of the guide wire of this invention.

FIG. 2 illustrates another embodiment of the guide wire of this invention, in which guide wire 30 has proximal portion 31 and distal portion 33. Distal portion 33 further has first tapering region 43, in which core wire 34 tapers from first diameter D1 to smaller diameter D2. Core wire 34 extends distally to second tapering region 44, in which core wire 34 has even smaller diameter D3. Over this region 44 and the region distal to this but proximal to region 45, are sixteen strands of 0.6064 cm (0.0025 inch) diameter nitinol wire, wound in a helical pattern to an overall diameter of 0.036 cm (0.014 inch) such as shown in FIG. 7 below. The strands are arrayed so that the diameter of the core and strands together in this region is slightly less than that of diameter D1. Core wire 34 extends to and terminates distally at distal end 33a through third tapering region 45. Thus, the distal most end of the core wire has a fourth, and smallest, diameter D4. This distal most end, i.e., tapering region 45 to distal end 33a, is coated with polymer coating 46. The polymer coating is applied so that the distal end has substantially the same diameter as the strand-wrapped section of the core wire adjacent to it. The entire distal region 33, as well as tapering region 43, are coated with radiopaque polymer 36, producing a distal portion with a diameter substantially the same as that of the central core, i.e., diameter D1. Lubricious coating 38 is applied over the distal portion of the guide wire, which is then ready for use.

Alternatively, polymer coating 46 can comprise in part radiopaque fillers as are known in the art. Radiopaque polymer 36 can optionally be omitted and diameters of strands 47 and polymer coating 46 increased to substantially equal diameter D1. In another embodiment, the polymer coating can be replaced in whole or in part by a radiopaque metallic coil as is known in the guide wire arts.

FIG. 3A illustrates another embodiment of the guide wire of this invention, in which guide wire 20 has proximal portion 21, distal portion 23, and tapering region 22. The distal portion can be flat, round, or be non-uniform in cross section as described in connection with FIG. 1A. Similar to the embodiment shown in FIG. 1A, diameter D1 of the proximal portion of central core 24 is larger than diameter D2 of the distal portion. Central core 24 does not extend to distal tip 23a, as it did in the embodiment shown in FIG. 1A, but instead truncates nearer tapering region 22, a distance away from distal tip 23a. Central core 24 is attached at region 25a to helically wound strands 25 of metal. In one embodiment sixteen strands of 0.0025 cm (0.001 inch) diameter nitinol are used, wound in a helical pattern to form a tube approximately 0.013 cm (0.005 inch) in outside diameter. The strands are attached using adhesives, soldering, welding, or a tubular band (not shown) can be used to crimp the strands to the central core, or other means. For a guide wire about 300 cm in length, length of strands 25 is about 25 cm. The helically wound strands have more strength than a comparable wire of conventional construction where a monofilament core of approximately 0.076 cm (0.003 inch) diameter would be used in the vicinity of the distal tip. In the examples given above the cross sectional area of the monofilament core is approximately 55% of that of the stranded construction.

Polymer coating 26 is applied over the entire guide wire, resulting in the full length of the guide wire having a constant diameter. That is, the diameter of the polymer coated distal portion is the same as diameter as the polymer coated proximal portion of the central core. The coating may be radiopaque due to fillers added to the polymer as described above. In addition, lubricious coating 28 is applied over the distal portion of the guide wire. In another embodiment, the polymer coating can be replaced in whole or in part by a radiopaque metallic coil as is known in the guide wire arts.

Figure 3B:
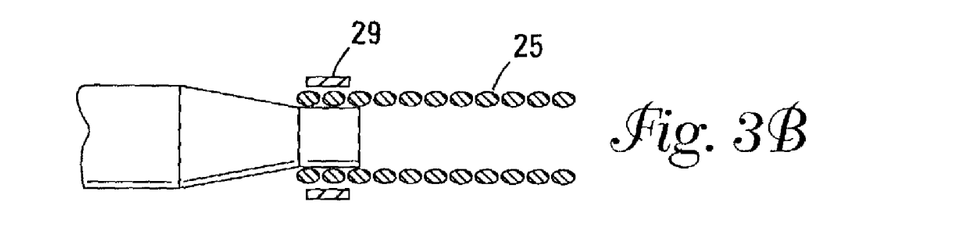
Figure 3C:
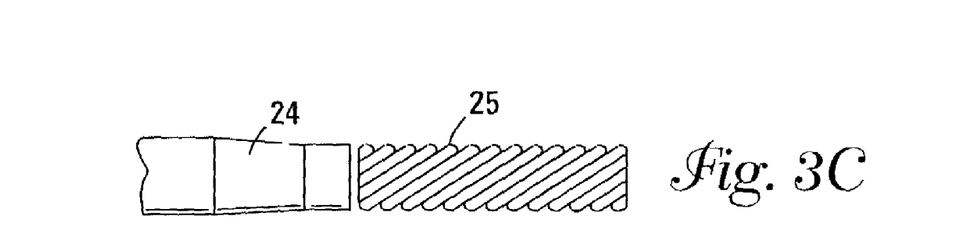
Figure 3D:
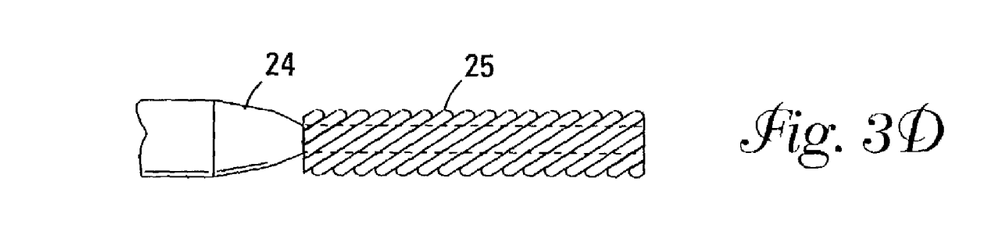

FIG. 3B shows more detail of core/strand connection for a wire similar to FIG. 3A. Crimp band 29 is shown and is optional, and can be made of stainless steel, platinum, platinum/iridium, titanium, or other materials than are malleable and strong. A preferred combination is a stainless steel core with nitinol strands. FIG. 3C shows strands 25 that are end to end with core wire 24. Tensile strength is delivered by polymer coatings. In a preferred embodiment, stranded wires have a central polymer core within the tubular stranded structure so as to prevent collapse of the strands within the central tubular region. FIG. 3D shows core wire 24 extending to the distal end and strands 25 over the core. This figure is similar to FIG. 1A, but strands are not near the surface of the wire.

Figure 4:
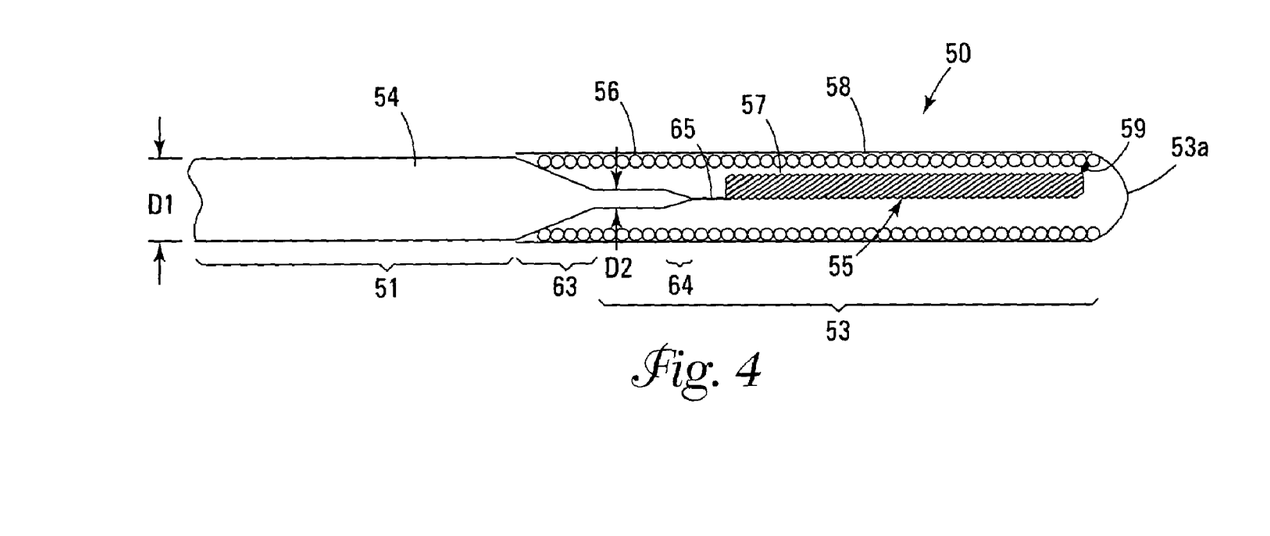
FIG. 4 is a cross-sectional view of another embodiment of the guide wire of this invention.

FIG. 4 illustrates another embodiment of a guide wire of this invention, in which guide wire 50 has proximal portion 51 and distal portion 53, terminating at distal tip 53a. Proximal portion 51 of core wire 54 has first diameter D1 and first tapering region 63. The central core tapers through region 63 distally to a smaller diameter D2, ultimately tapering again at region 64 to flattened end 65 of the central core. Attached to flattened end 65 are strands 55 of nitinol having a radiopaque coil 56 disposed over it. In one embodiment eight strands of 0.038 cm (0.0015 inch) diameter nitinol are used to form the stranded portion. The strands are attached to flattened end 65 by welding, soldering, adhesive bonding, or with heat shrink tubing. An optional weld 59 can attach the strands 55 to the coil 56. The entire length of strands 55 or only a portion may have the radiopaque coil around it. Disposed over the distal portion 53 and tapered portion 63 is a polymer layer 57 and disposed over that is lubricious coating 58. Polymer coating may optionally be applied to the region inside radiopaque coil 56 and around the core and strands. The strands may optionally have polymer within the interior of the tubular stranded structure.

Figure 5A:
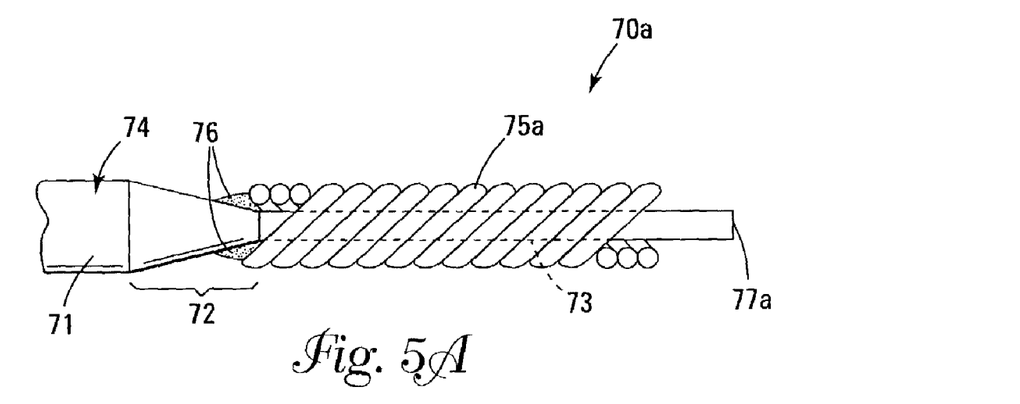
FIGS. 5A to 5C are side views of the distal ends of various embodiments of the guide wire of this invention.
Figure 5B:
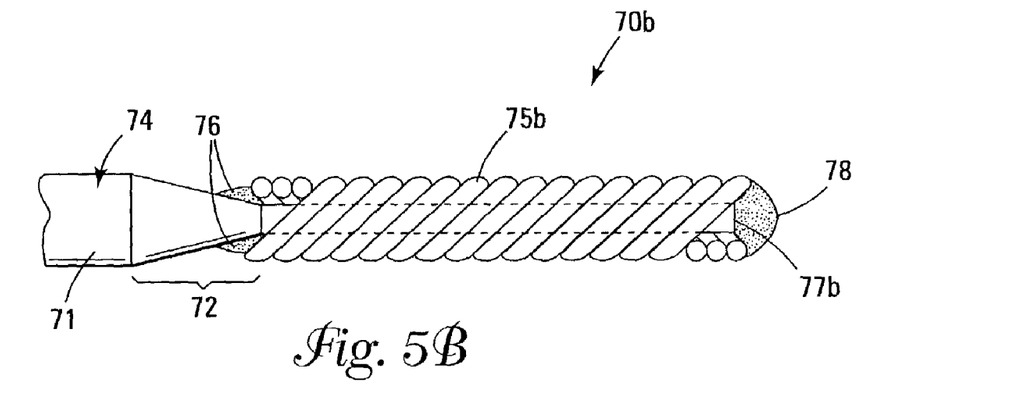
Figure 5C:
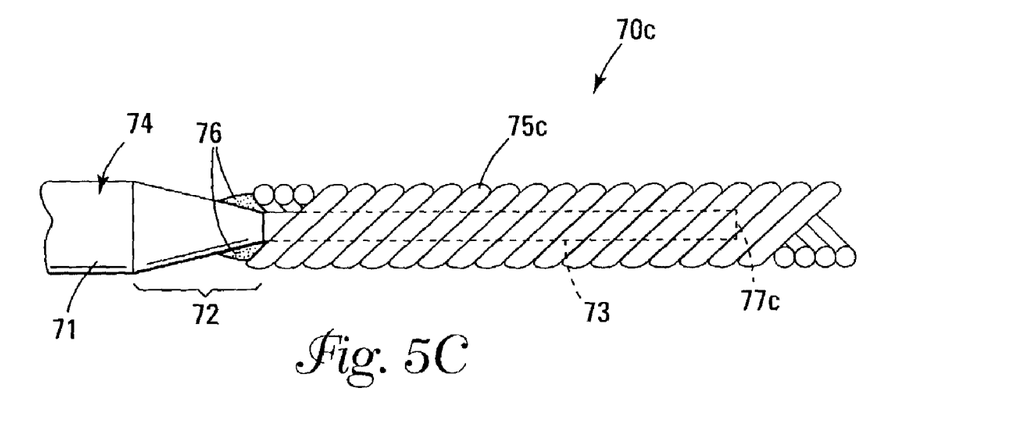

It is recognized that the relative position of core and strands at the tip of the wires disclosed herein can be varied. FIGS. 5A to 5C illustrate various distal tip stranded configurations for guide wires 70a, 70b, and 70c, respectively. Central core 74 is the same for each guide wire, having proximal portion 71, distal portion 73, and tapering region 72. In FIG. 5A, stranded material 75a is attached to tapering region 72 by means of a weld 76 and does not extend all the way to distal end 77a. FIG. 5B is similar to FIG. 5A, and shows guide wire 70b having stranded material 75b attached to tapering region 72 by a weld 76 and attached to core distal end 77b by a weld 78. In FIG. 5C, guide wire 70c has stranded material 75c attached to tapering region 72 by a weld 76 and extending beyond distal end 77c.

Figure 6:
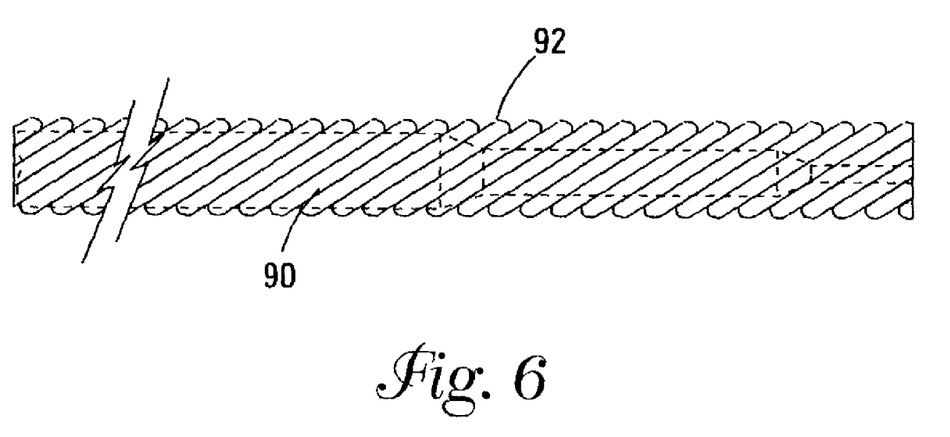
FIG. 6 is a side view of another embodiment of the guide wire of this invention.

FIG. 6 illustrates an alternate embodiment of the present invention. Strands 92 run full length, can be attached to the core 90 at proximal and distal ends of the core wire and optionally at intermediate locations. The core wire has geometries at the distal end as in FIGS. 1A to 1H or FIGS. 3B to 3D. The polymer can be inside the stranded tubular core, around the core (like FIG. 1A), and over the strands. Preferably, a lubricious coating is disposed on the polymer. The advantages of this guide wire include tremendous strength over its entire length; no bonds/welds/transitions to catch on when passing a catheter over the wire; and great torque right to the tip. This embodiment may have less friction with catheter due to bumpy smooth surface of wire.

FIG. 7 illustrates strands 105 that are helically wound around central core 104. The central core can be polymer, composite, ceramic, metal, or any other suitable substrate that allows for uniform winding of the strands. Central core 104 can be incorporated into some of the guide wires shown herein or can be removed to allow strands 105 to be used in other structures shown herein. One or more strands can be comprised of radiopaque materials such as platinum, platinum/iridium alloy, tungsten, clad composite materials known as drawn filled tubing (DFT), coated materials, or other materials as are known in the art.

Method of Manufacture

A guide wire according to this invention can be made by winding wires of the desired diameter around a support mandrel or core. Individual wires are wound onto spools, which are loaded into a stranding machine. Each wire is pulled under tension through the apex of the stranding machine and wrapped around a support mandrel. For example, a helical wind is desirable. Wires wound in this way are oriented at an angle of 10 to 80 degrees relative to the longitudinal axis of the support mandrel.

Wire is released from the spools and spirally wound around the support mandrel as it is fed through the stranding machine. Rollers may be used to contact the wires prior to and after the apex to control how tightly the wires are wrapped onto the support mandrel. For some materials, a heater is used post-apex for shape retention. The temperatures used depend upon the composition of the wires. For example, nitinol is processed from 450° C. to 550° C. Some metals, such as platinum, gold, or annealed stainless steel are sufficiently pliable to forego the heat treatment. The stranded material/support mandrel is cut into lengths, and the strands are removed from the support mandrel. The stranded material is then trimmed to a desired length and fitted over the distal shaped end of the guide wire.

Figure 8:
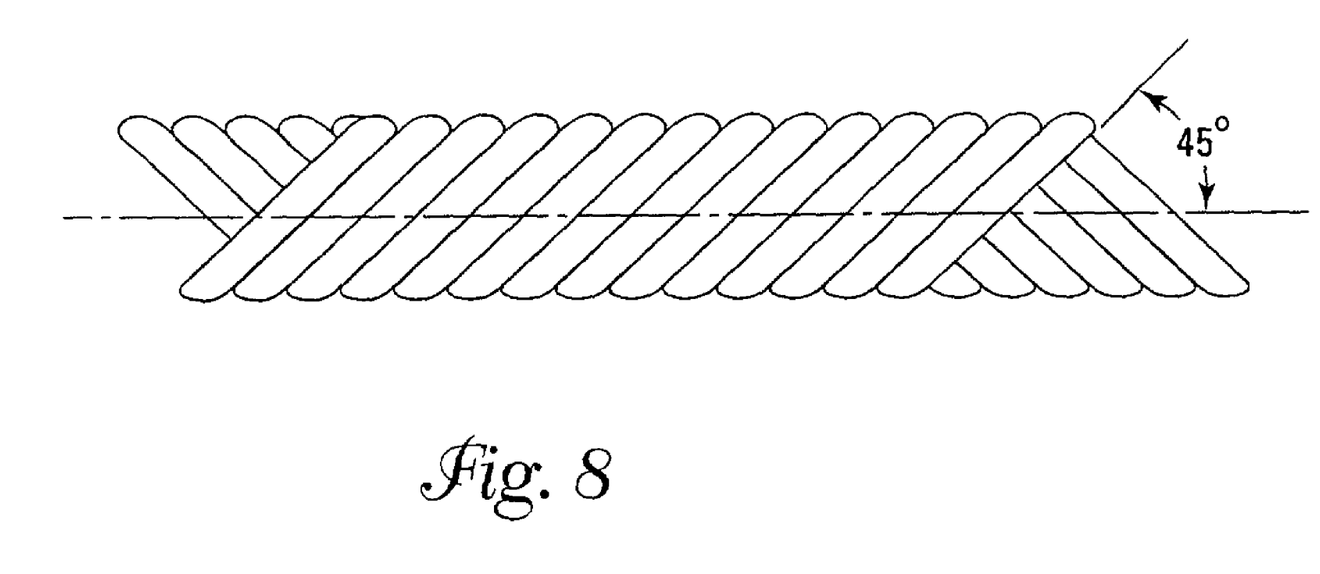
FIG. 8 is a side view of a section of stranded wires.

FIG. 8 illustrates six stranded wires where the angle θ (theta) is 45 degrees. This figure also shows a relatively tight helical wind. The amplitude of this wind is much different from that shown in FIG. 7, which is approximately 33 degrees. For the stranded wires used in this invention angles of 10 to 45 degrees are generally preferred, and angles of 15 to 30 degrees are particularly preferred. These angles provide good tip strength without danger of tip elongation and fracture during use.

The above description and the drawings are provided for the purpose of describing embodiments of the invention and are not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents.

What is claimed is:

1. A guide wire comprising:
    an elongate, flexible core having a proximal region, a proximal end, a distal region, and a distal end, and the distal region having a tapered portion;
    a single coil comprising 3 to 24 wire strands, each of the 3 to 24 wire strands being formed in a single helix and wrapped helically parallel to one another to thereby form the single coil, the single coil having a longitudinal central axis and an interior, and at least a portion of the tapered distal region of the core being disposed within the interior of the single coil;
    a polymer tie layer disposed on at least a portion of the wire strands; and
    a lubricious polymer layer disposed on the polymer tie layer, and
    wherein the angle between the wire strands and the longitudinal central axis is from 10 to 45 degrees.

2. A guide wire of claim 1, wherein the polymer tie layer is disposed on the entire distal end of the guide wire.

3. A guide wire of claim 1, wherein the guide wire further comprises a coil disposed at the distal end.

4. A guide wire of claim 3, wherein at least a portion of the coil is not covered by the polymer tie layer.

5. A guide wire of claim 1, wherein the guide wire further comprises a radiopaque tip disposed at the distal end.

6. A guide wire of claim 5, wherein the radiopaque tip comprises a polymer containing radiopaque material.

7. A guide wire of claim 1, wherein the polymer tie layer provides the only form of attachment between the wire strands and the core.

8. A guide wire of claim 1, wherein the wire strands are attached to the core by one or more solders, welds, swaging tubes, or adhesives.

9. A guide wire of claim 1, wherein the guide wire has a distal end and the core extends to the distal end of the guide wire.

10. A guide wire of claim 1, wherein the guide wire has a distal end and the core does not extend to the distal end of the guide wire.

11. A guide wire of claim 1, wherein the wire strands have distal ends and the core extends past the distal ends of the wire strands.

12. A guide wire of claim 1, wherein the length of the guide wire is from 30 to 350 cm.

13. A guide wire of claim 1, wherein the length of the guide wire is from 150 to 320 cm.

14. A guide wire of claim 1, wherein the guide wire has an outer diameter of from 0.013 to 0.097 cm.

15. A guide wire of claim 1, wherein the guide wire comprises 5 to 8 wire strands.

16. A guide wire of claim 1, wherein the wire strands have lengths of from 1 to 80 cm.

17. A guide wire of claim 1, wherein the wire strands have outer diameters of from 0.0025 to 0.025 cm.

18. A guide wire of claim 1, wherein the tapered distal region of the core has a length of from 5 to 80 cm.

19. A guide wire of claim 1, wherein the angle between the wire strands and the central longitudinal axis is from 15 to 30 degrees.

20. A guide wire of claim 1, wherein the entire core is disposed within the interior of the single coil.

21. A guide wire comprising:
    an elongate, flexible core having a proximal region, a proximal end, a distal region, and a distal end, and the distal region having a tapered portion;
    a single coil comprising 3 to 24 wire strands, each of the 3 to 24 wire strands being formed in a single helix and wrapped helically parallel to one another to thereby form the single coil, the single coil having a longitudinal central axis and an interior, and at least a portion of the tapered distal region of the core being disposed within the interior of the single coil; and
    a polymer tie layer disposed on at least a portion of the wire strands,
    wherein the polymer tie layer provides the only form of attachment between the wire strands and the core, and
    wherein the angle between the wire strands and the longitudinal central axis is from 10 to 45 degrees.

22. A guide wire of claim 21, wherein the polymer tie layer is disposed on the entire distal end of the guide wire.

23. A guide wire of claim 21, wherein the guide wire further comprises a second coil disposed at the distal end.

24. A guide wire of claim 23, wherein at least a portion of the second coil is not covered by the polymer tie layer.

25. A guide wire of claim 21, wherein the guide wire further comprises a radiopaque tip disposed at the distal end.

26. A guide wire of claim 25, wherein the radiopaque tip comprises a polymer containing radiopaque material.

27. A guide wire of claim 21, wherein the guide wire has a distal end and the core extends to the distal end of the guide wire.

28. A guide wire of claim 21, wherein the guide wire has a distal end and the core does not extend to the distal end of the guide wire.

29. A guide wire of claim 21, wherein the wire strands have distal ends and the core extends past the distal ends of the wire strands.

30. A guide wire of claim 21, wherein the length of the guide wire is from 30 to 350 cm.

31. A guide wire of claim 21, wherein the length of the guide wire is from 150 to 320 cm.

32. A guide wire of claim 21, wherein the guide wire has an outer diameter of from 0.013 to 0.097 cm.

33. A guide wire of claim 21, wherein the guide wire comprises 5 to 8 wire strands.

34. A guide wire of claim 21, wherein the wire strands have lengths of from 1 to 80 cm.

35. A guide wire of claim 21, wherein the wire strands have outer diameters of from 0.0025 to 0.025 cm.

36. A guide wire of claim 21, wherein the tapered distal region of the core has a length of from 5 to 80 cm.

37. A guide wire of claim 21, wherein the angle between the wire strands and the central longitudinal axis is from 15 to 30 degrees.

38. A guide wire of claim 21, wherein the entire core is disposed within the interior of the single coil.

39. A guide wire comprising:
an elongate, flexible core having a proximal region, a proximal end, a distal region, and a distal end;
a single coil comprising 3 to 24 wire strands, each of the 3 to 24 wire strands being formed in a single helix and wrapped helically parallel to one another to thereby form the single coil, the single coil having a longitudinal central axis and an interior, and the single coil being disposed distal to the distal end of the elongate, flexible core; and
a polymer tie layer disposed on at least a portion of the wire strands and at least a portion of the elongate, flexible core, and
wherein the angle between the wire strands and the longitudinal central axis is from 10 to 45 degrees.

* * * * *